United States Patent
Yamaguchi et al.

(10) Patent No.: US 11,046,965 B2
(45) Date of Patent: Jun. 29, 2021

(54) METHOD OF PRODUCING TRANSFORMED CELLS OF RUBBER-PRODUCING PLANT

(71) Applicant: SUMITOMO RUBBER INDUSTRIES, LTD., Kobe (JP)

(72) Inventors: Haruhiko Yamaguchi, Kobe (JP); Yukino Inoue, Kobe (JP); Teruhiko Terakawa, Yokohama (JP); Tsubasa Yano, Yokohama (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 0 days.

(21) Appl. No.: 16/439,289

(22) Filed: Jun. 12, 2019

(65) Prior Publication Data
US 2020/0017866 A1    Jan. 16, 2020

(30) Foreign Application Priority Data

Jul. 10, 2018 (JP) .............................. JP2018-130945

(51) Int. Cl.
*C12N 15/82* (2006.01)
(52) U.S. Cl.
CPC ................................ *C12N 15/8207* (2013.01)
(58) Field of Classification Search
CPC ... A01H 6/38; C12N 15/8207; C12N 15/8027
See application file for complete search history.

(56) References Cited

U.S. PATENT DOCUMENTS

2002/0066121 A1* 5/2002 Kosegi ............... C12N 15/8207
800/278

FOREIGN PATENT DOCUMENTS

JP    2010-161989 A    7/2010

OTHER PUBLICATIONS

Terakawa et al. "Efficient Whisker-mediated Gene Transformation in a Combination with Supersonic Treatment," Breeding Science 55: 465-468 (2005).*
Montoro et al. "Effect of exogenous calcium on Agrobacterium tumefaciens-mediated gene transfer in Hevea brasiliensis (rubber tree) friable calli", Plant Cell Reports (2000) 19:851-855.*
Asad et al., "Silicon Carbide Whisker-mediated Plant Transformation," Properties and Applications of Silicon Carbide, Apr. 2001, pp. 345-358 (16 pages total).
Jayashree et al., "Genetic transformation and regeneration of rubber tree (*Hevea brasiliensis* Muell. Arg) transgenic plants with a constitute version of an anti-oxidative stress superoxide dismutase gene," Plant Cell Rep, vol. 22, 2003, pp. 201-209.
Montoro et al., "Effect of exogenous calcium on *Agrobacterium tumefaciens*-mediated gene transfer in *Hevea brasiliensis* (rubber tree) friable calli," Plant Cell Reports, vol. 19, 2000, pp. 851-855.
Montoro et al., "Production of *Hevea brasiliensis* transgenic embryogenic callus lines by *Agrobacterium tumefaciens*: roles of calcium," Plant Cell Rep, vol. 21, 2003, pp. 1095-1102.
Terakawa et al., "Efficient Whisker-mediated Gene Transformation in a Combination with Supersonic Treatment," Breeding Science, vol. 55, 2005, pp. 465-468.
Wang et al., "Whisker-Mediated Plant Transformation: An Alternative Technology," In Vitro Cell. Dev. Biol., vol. 31, Apr. 1995, XP-002103974, pp. 101-104.

* cited by examiner

*Primary Examiner* — Susan McCormick Ewoldt
(74) *Attorney, Agent, or Firm* — Birch, Stewart, Kolasch & Birch, LLP

(57) ABSTRACT

The present invention provides a method which can replace *Agrobacterium* techniques and which can efficiently produce transformed cells of a rubber-producing plant. The present invention relates to a method of producing transformed cells of a rubber-producing plant, which includes steps a) to e).

4 Claims, No Drawings

METHOD OF PRODUCING TRANSFORMED CELLS OF RUBBER-PRODUCING PLANT

TECHNICAL FIELD

The present invention relates to a method of producing transformed cells of a rubber-producing plant.

BACKGROUND ART

Natural rubber may be obtained by cultivating rubber-producing plants, such as para rubber tree (*Hevea brasiliensis*) belonging to the family Euphorbiaceae or Indian rubber tree (*Ficus elastica*) belonging to the family Moraceae, whose laticifer cells biosynthesize natural rubber, and manually harvesting the natural rubber from the plants.

At present, *Hevea brasiliensis* is the only source for the natural rubber used in industrial rubber products. *Hevea brasiliensis* is a plant that can grow in limited regions, including Southeast Asia and South America. Moreover, *Hevea brasiliensis* trees take about seven years from planting to grow mature enough to yield rubber, and they yield natural rubber only for a period of 20 to 30 years. Demand for natural rubber is expected to grow in the future, especially in developing countries, but for the reasons discussed above it is difficult to greatly increase natural rubber production from *Hevea brasiliensis*. There is therefore concern that natural rubber sources will dry up, and a need exists to improve natural rubber yield from *Hevea brasiliensis*.

Possible methods for improving the yield from *Hevea brasiliensis* include the use of conventional artificial crossing or mutation techniques. However, such methods have difficulty in efficiently imparting desired characteristics and thus are unlikely to be feasible. Therefore, it is believed that methods of using genetic transformation techniques to improve rubber trees will come into use in the future.

Many genetic transformation techniques for rubber-producing plants, including *Hevea brasiliensis*, involve the use of *Agrobacterium* (see, for example, Patent Literature 1).

CITATION LIST

Patent Literature

Patent Literature 1: JP 2010-161989 A

SUMMARY OF INVENTION

Technical Problem

However, the present inventors have found as a result of experimentation that *Agrobacterium* techniques provide varied gene transfer efficiencies depending on the compatibility between the microorganism and plant, and further are not suitable for transforming some plant species (e.g. rice and soy).

The present invention aims to solve the problem and provide a method which can replace *Agrobacterium* techniques and which can efficiently produce transformed cells of a rubber-producing plant.

Solution to Problem

As a result of extensive research and experimentation, the present inventors successfully produced transformed cells of a rubber-producing plant using whisker techniques instead of *Agrobacterium* techniques.

The inventors then conducted studies on the conditions for more efficiently producing transformed cells of a rubber-producing plant and found that it is important for high gene transfer efficiency to: use a small mass of cultured cells (cultured cell cluster); perform centrifugation and sonication; and restore the damaged cells without removing the whisker. Based on this finding, the inventors conducted further studies, which have provided a number of findings leading to the present invention.

Specifically, the present invention relates to a method of producing transformed cells of a rubber-producing plant, the method including the following steps a) to e):
  a) culturing a tissue fragment from a rubber-producing plant in a medium containing a plant growth hormone to obtain a 5.0 mm or smaller mass of cultured cells;
  b) dispersing the cultured cells obtained in step a) and a whisker in a liquid and then adhering the whisker to the cultured cells by centrifugation; followed by
  c) damaging the cultured cells by the whisker under sonication and introducing a foreign gene into the cells; followed by
  d) restoring the damaged cells without removing the whisker; followed by
  e) screening transformed cells with an antibiotic.

Preferably, the whisker is made of potassium titanate.
Preferably, step d) is carried out for at least 120 hours.
Preferably, the antibiotic used in step e) is kanamycin at a concentration of 10 mg/L or lower.
Preferably, the cultured cells are in the form of callus.
Preferably, the rubber-producing plant is at least one selected from the group consisting of plants of the genera *Hevea*, *Taraxacum*, and *Parthenium*.

Advantageous Effects of Invention

The method of producing transformed cells of a rubber-producing plant according to the present invention which includes steps a) to e) can efficiently produce transformed cells of a rubber-producing plant.

DESCRIPTION OF EMBODIMENTS

The method of producing transformed cells of a rubber-producing plant according to the present invention (hereinafter also referred to as inventive method) includes the following steps a) to e):
  a) culturing a tissue fragment from a rubber-producing plant in a medium containing a plant growth hormone to obtain a 5.0 mm or smaller mass of cultured cells;
  b) dispersing the cultured cells obtained in step a) and a whisker in a liquid and then adhering the whisker to the cultured cells by centrifugation; followed by
  c) damaging the cultured cells by the whisker under sonication and introducing a foreign gene into the cells; followed by
  d) restoring the damaged cells without removing the whisker; followed by
  e) screening transformed cells with an antibiotic.

As used herein, the term "cultured cells (cultured cell cluster)" refers to plant cells (plant cell cluster) produced by culturing a tissue fragment (tissue) from a plant, and more specifically refers to callus.

As used herein, the term "callus" refers to undifferentiated plant cells or an undifferentiated plant cell cluster.

As used herein, the term "transformed cells" refers to cells transfected with a foreign gene.

As used herein, the term "foreign gene" refers to a gene that is introduced into a host organism by gene transfer.

The rubber-producing plant may be any plant capable of producing natural rubber, and examples include the genus *Hevea*, e.g. *Hevea brasiliensis*; the genus *Sonchus*, e.g. *Sonchus oleraceus*, *Sonchus asper*, and *Sonchus brachyotus*; the genus *Solidago*, e.g. *Solidago altissima*, *Solidago virgaurea* subsp. *asiatica*, *Solidago virgaurea* subsp. *leipcarpa*, *Solidago virgaurea* subsp. *leipcarpa* f. *paludosa*, *Solidago virgaurea* subsp. *gigantea*, and *Solidago gigantea* Ait. var. *leiophylla* Fernald; the genus *Helianthus*, e.g. *Helianthus annus*, *Helianthus argophyllus*, *Helianthus atrorubens*, *Helianthus debilis*, *Helianthus decapetalus*, and *Helianthus giganteus*; the genus *Taraxacum*, e.g. dandelion (*Taraxacum*), *Taraxacum venustum* H. Koidz, *Taraxacum hondoense* Nakai, *Taraxacum platycarpum* Dahlst, *Taraxacum japonicum*, *Taraxacum officinale* Weber, and *Taraxacum kok-saghyz*; the genus *Ficus*, e.g. *Ficus carica*, *Ficus elastica*, *Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis*; the genus *Parthenium*, e.g. *Parthenium argentatum*, and *Parthenium hysterophorus*, *Ambrosia artemisiifolia*; and lettuce (*Lactuca sativa*) and *Lactuca serriola*. Preferably, the rubber-producing plant is at least one selected from the group consisting of plants of the genera *Hevea*, *Taraxacum*, and *Parthenium*, and more preferably from the group consisting of *Hevea brasiliensis*, *Taraxacum kok-saghyz*, and *Parthenium argentatum*. It is particularly preferably a plant of the genus *Hevea* (*Hevea brasiliensis*), among others.

Step a):

Step a) includes culturing a tissue fragment from a rubber-producing plant in a medium containing a plant growth hormone to obtain a 5.0 mm or smaller mass of cultured cells.

In step a), preferably, for example, callus (cultured cells) may be prepared by culturing a tissue fragment from a rubber-producing plant in a medium containing a plant growth hormone. Thus, callus may be induced from a tissue fragment from a rubber-producing plant. Since it is well known how to induce callus from a tissue fragment from a rubber-producing plant, a process of inducing callus will be described below as one non-limiting example of such methods. A person skilled in the art can induce callus from a tissue fragment from a rubber-producing plant in an appropriate manner.

<Induction Process>

The following describes how to prepare callus (induction process).

An exemplary induction process includes culturing a tissue fragment (tissue) from a rubber-producing plant (hereinafter also referred to simply as plant) in an induction medium containing a plant growth hormone and a carbon source to induce callus.

Any tissue fragment may be used. Preferred is at least one selected from the group consisting of leaves, stems, roots, buds, petals, cotyledons, hypocotyls, anthers, and seeds, and more preferably from leaves and stems.

In the induction process, the surface of the plant tissue fragment is first cleaned. When an inner tissue of a plant is used as the tissue fragment, it may be cleaned, e.g. with a cleanser or in water containing about 0.1% of a surfactant. The surface of a tissue fragment such as leaf, if used, is preferably cleaned with a soft sponge.

Next, the tissue fragment is disinfected or sterilized. The disinfection or sterilization may be carried out using known disinfectants or sterilizing agents, preferably ethanol, benzalkonium chloride, or an aqueous sodium hypochlorite solution.

Then, the disinfected or sterilized tissue fragment is cultured in an induction medium containing a plant growth hormone and a carbon source to induce callus. The induction medium may be either a liquid or a solid, but solid culture is preferred because callus formation is facilitated by plating on the medium. When the induction medium is a liquid medium, static culture or shake culture may be performed.

Examples of the plant growth hormone include auxin plant hormones and/or cytokinin plant hormones.

The auxin plant hormones may be exemplified by 2,4-dichlorophenoxyacetic acid, naphthaleneacetic acid, indolebutyric acid, indoleacetic acid, indolepropionic acid, chlorophenoxyacetic acid, naphthoxyacetic acid, phenylacetic acid, 2,4,5-trichlorophenoxyacetic acid, para-chlorophenoxyacetic acid, 2-methyl-4-chlorophenoxyacetic acid, 4-fluorophenoxyacetic acid, 2-methoxy-3,6-dichlorobenzoic acid, 2-phenyl acid, picloram, and picolinic acid. Among the foregoing, 2,4-dichlorophenoxyacetic acid, naphthaleneacetic acid, and indolebutyric acid are preferred, with 2,4-dichlorophenoxyacetic acid or naphthaleneacetic acid being more preferred. Still more preferred for plants of the genus *Sonchus*, particularly *Sonchus oleraceus*, is naphthaleneacetic acid, while for plants of the genus *Hevea*, particularly *Hevea brasiliensis*, 2,4-dichlorophenoxyacetic acid is still more preferred.

The cytokinin plant hormones may be exemplified by benzyladenine, kinetin, zeatin, benzylaminopurine, isopentenylaminopurine, thidiazuron, isopentenyladenine, zeatin riboside, and dihydrozeatin. Among the foregoing, benzyladenine, kinetin, and zeatin are preferred, with benzyladenine or kinetin being more preferred. Still more preferred for plants of the genus *Sonchus*, particularly *Sonchus oleraceus*, is benzyladenine, while for plants of the genus *Hevea*, particularly *Hevea brasiliensis*, kinetin or benzyladenine is still more preferred.

Any carbon source may be used, including sugars such as sucrose, glucose, trehalose, fructose, lactose, galactose, xylose, allose, talose, gulose, altrose, mannose, idose, arabinose, apiose, and maltose. Among the foregoing, sucrose or glucose is preferred, with sucrose being more preferred.

The induction medium may be prepared by adding a plant growth hormone to any of the following base media: basal media such as White's medium (disclosed on pp. 20-36 of Shokubutsu Saibo Kogaku Nyumon (Introduction to Plant Cell Engineering), Japan Scientific Societies Press), Heller's medium (Heller R, Bot. Biol. Veg. Paris 14, 1-223 (1953)), SH medium (Schenk and Hildebrandt medium), MS medium (Murashige and Skoog medium) (disclosed on pp. 20-36 of Shokubutsu Saibo Kogaku Nyumon (Introduction to Plant Cell Engineering), Japan Scientific Societies Press), LS medium (Linsmaier and Skoog medium) (disclosed on pp. 20-36 of Shokubutsu Saibo Kogaku Nyumon (Introduction to Plant Cell Engineering), Japan Scientific Societies Press), Gamborg medium, B5 medium (disclosed on pp. 20-36 of Shokubutsu Saibo Kogaku Nyumon (Introduction to Plant Cell Engineering), Japan Scientific Societies Press), MB medium, and WP medium (Woody Plant: for woody plants) (the disclosures of the foregoing documents are incorporated by reference herein), and modified basal media obtained by altering the composition of the basal media. It is preferred to add a plant growth hormone to MS medium, B5 medium, or WP medium, among others. It is also preferred for the induction medium to contain an auxin plant hormone and/or a cytokinin plant hormone which are suitable for callus maintenance and promotion of cell division.

The induction medium may contain at least one selected from the group consisting of jasmonic acid and monoterpene compounds.

Examples of such monoterpene compounds include D-limonene, α-pinene, β-pinene, l-menthol, geraniol, carane, pinane, myrcene, ocimene, and cosmene. Among the foregoing, D-limonene or α-pinene is preferred.

When the induction medium is prepared as a solid medium, the medium may be converted to a solid using a solidifying agent. Non-limiting examples of the solidifying agent include agar, gellan gum (e.g. Gelrite, Phytagel), agarose, gelatin, and silica gel.

The suitable composition and culture conditions of the induction medium vary depending on the type of plant and on whether the medium is a liquid medium or a solid medium, but the composition, especially for plants of the genus *Sonchus*, particularly *Sonchus oleraceus*, and plants of the genus *Hevea*, particularly *Hevea brasiliensis*, is usually as follows.

The carbon source concentration in the induction medium is preferably at least 0.1 massa, more preferably at least 1 mass %. The carbon source concentration is preferably not more than 10 mass %, more preferably not more than 6 mass %, still more preferably not more than 3 mass %. As used herein, the carbon source concentration means the sugar concentration.

The auxin plant hormone concentration in the induction medium is preferably at least 0 mg/L, more preferably at least $1\times10^{-3}$ mg/L, still more preferably at least 0.05 mg/L, particularly preferably at least 0.5 mg/L. For plants of the genus *Hevea*, particularly *Hevea brasiliensis*, it is most preferably at least 1.5 mg/L. The auxin plant hormone concentration is preferably not more than 20 mg/L, more preferably not more than 10 mg/L, still more preferably not more than 2.5 mg/L.

The cytokinin plant hormone concentration in the induction medium is preferably at least 0 mg/L, more preferably at least $1\times10^{-3}$ mg/L, still more preferably at least 0.1 mg/L, particularly preferably at least 0.5 mg/L. For plants of the genus *Hevea*, particularly *Hevea brasiliensis*, it is most preferably at least 0.8 mg/L. The cytokinin plant hormone concentration is preferably not more than 15 mg/L, more preferably not more than 10 mg/L, still more preferably not more than 3 mg/L.

The pH of the induction medium is preferably 4.0 to 10.0, more preferably 5.6 to 6.5, still more preferably 5.7 to 5.8. The culture temperature is preferably 0 to 40° C., more preferably 20 to 30° C. Culture may be carried out in the dark or in the light, and the illuminance is preferably 0 to 100,000 lx, more preferably 0 to 0.1 lx. The culture time is not particularly critical, but culture for 1 to 10 weeks is preferred.

As used herein, the pH of the solid medium means the pH of the medium that incorporates all the components except the solidifying agent. As used herein, the dark means that the illuminance is 0 to 0.1 lx, while the light means that the illuminance is more than 0.1 lx.

The solidifying agent concentration in the induction medium used as a solid medium is preferably at least 0.1 mass %, more preferably at least 0.2 mass %. The solidifying agent concentration is preferably not more than 2 mass %, more preferably not more than 1.1 mass %, still more preferably not more than 0.6 mass %.

Among the conditions indicated above, it is particularly preferred for plants of the genus *Sonchus*, particularly *Sonchus oleraceus*, that the auxin plant hormone is naphthaleneacetic acid at a concentration of 0.5 to 2.5 mg/L, the cytokinin plant hormone is benzyladenine, and the culture temperature is 20 to 26° C.

Among the conditions indicated above, it is particularly preferred for plants of the genus *Hevea*, particularly *Hevea brasiliensis*, that the auxin plant hormone is 2,4-dichlorophenoxyacetic acid at a concentration of 1.5 to 2.5 mg/L, and the cytokinin plant hormone is benzyladenine at a concentration of 0.8 to 3 mg/L.

As described above, callus can be induced by culturing the disinfected or sterilized tissue fragment in the induction medium.

Since step a) involves culturing a tissue fragment from a rubber-producing plant in a medium containing a plant growth hormone to obtain a 5.0 mm or smaller mass of cultured cells, it may be unsatisfactory to only perform the induction process according to which a tissue fragment from a rubber-producing plant is cultured in a medium containing a plant growth hormone to prepare callus (cultured cells).

When the callus induced in the induction process has a predetermined size or smaller, it may be used directly in the subsequent step b). When the induced callus is larger than the predetermined size, the induction process needs to be followed by a size adjustment process as described below.

<Size Adjustment Process>

Any size adjustment process that can adjust the callus to a predetermined size or smaller may be used.

This process may be carried out, for example, by cutting the callus with a knife or other means or crushing the callus using a crusher or other means. In order to reduce damage to the callus, it is preferred to place the callus statically on a metal mesh, and apply force to the callus on the mesh to pass the callus through the openings of the mesh so that it is adjusted to a desired size.

The size of the mass of cultured cells (cultured cell cluster) obtained in step a) (and used in step b)) is 5.0 mm or smaller, preferably 3.0 mm or smaller, more preferably 1.0 mm or smaller. In the present invention, since the use of a small mass of cultured cells (cultured cell cluster) enables an increase in gene transfer efficiency, the lower limit of the size is not particularly critical. For easy handling, it is preferably 0.1 mm or larger, more preferably 0.2 mm or larger, still more preferably 0.3 mm or larger, particularly preferably 0.4 mm or larger.

The size of the mass of cultured cells (cultured cell cluster) means the longest diameter of the mass of cultured cells (cultured cell cluster). The longest diameter means the maximum length obtained when the mass of cultured cells (cultured cell cluster) is projected onto a projection plane while varying the direction of the mass of cultured cells (cultured cell cluster) relative to the projection plane. For example, it is the length of the longest side of a rectangle, or the diameter of a disk.

The size of the mass of cultured cells (cultured cell cluster) is the average of the sizes of 100 masses of cultured cells (cultured cell clusters).

Step b):

Step b) includes dispersing the cultured cells obtained in step a) and a whisker in a liquid and then adhering the whisker to the cultured cells by centrifugation.

Step b) is characterized by: using a small mass of cultured cells (cultured cell cluster); and centrifuging the cultured cells together with a whisker. These features enable an increase in gene transfer efficiency.

As used herein, the term "whisker" refers to an acicular single crystal (acicular single crystal fiber).

Any whisker that can damage cells may be used.

The average fiber diameter of the whisker is preferably 0.01 µm or more, more preferably 0.05 µm or more, still more preferably 0.1 µm or more, but is preferably 10 µm or less, more preferably 5 µm or less, still more preferably 1 µm or less. When the average fiber diameter of the whisker falls within the range indicated above, more suitable effects can be obtained.

The average fiber length of the whisker is preferably 1 µm or more, more preferably 3 µm or more, still more preferably 5 µm or more, but is preferably 100 µm or less, more preferably 60 µm or less, still more preferably 30 µm or less. When the average fiber length of the whisker falls within the range indicated above, more suitable effects can be obtained.

The average fiber diameter and average fiber length of the whisker herein can be measured by image analysis using scanning electron micrographs.

The whisker may be made of any material that can damage cells. Examples include potassium titanate, calcium carbonate, aluminum borate, silicon nitride, zinc oxide, basic magnesium sulfate, magnesia, magnesium borate, titanium diboride, carbon graphite, calcium sulfate, sapphire, and silicon carbide. Among the foregoing, potassium titanate, calcium carbonate, aluminum borate, and silicon carbide are preferred, with potassium titanate being more preferred.

The whisker is preferably disinfected, e.g. with ethanol or ultraviolet light.

In step b), the cultured cells obtained in step a) and whisker are dispersed in a liquid to prepare a cultured cell/whisker dispersion.

The cultured cell/whisker dispersion may be prepared by any method capable of preparing a dispersion in which the cultured cells and whisker are dispersed, such as, for example, by: introducing and mixing both the cultured cells and whisker into a liquid; or introducing and mixing the whisker into a liquid in which the cultured cells are dispersed; or introducing and mixing the cultured cells into a liquid in which the whisker is dispersed; or mixing a liquid in which the cultured cells are dispersed with a liquid in which the whisker is dispersed. Among these methods, mixing a liquid in which the cultured cells are dispersed with a liquid in which the whisker is dispersed is preferred in order to obtain more suitable effects.

The liquid (dispersion medium used in step b)) may be any liquid, including distilled water, isotonic solutions, buffers, and tissue culture media. Exemplary isotonic solutions include liquids prepared by adding inorganic salts (e.g. KCl, NaCl, $CaCl_2$, $MgCl_2$) at a concentration of 0.01 to 7M, preferably 0.5 to 2M. Exemplary buffers include phosphate buffer, Tris buffer, and MES buffer. Exemplary tissue culture media include the media listed above. Among these liquids, tissue culture media are preferred in order to avoid an adverse effect on the proliferation (growth) of the cultured cells of the plant and obtain more suitable effects.

The dispersion medium used in step b) is preferably a liquid prepared by adding a carbon source and a plant growth hormone to a basal medium, preferably MS medium. Suitable carbon sources and plant growth hormones are those listed for the induction medium.

In particular, it is particularly preferred that the auxin plant hormone is 2,4-dichlorophenoxyacetic acid at a concentration of 1 to 3 mg/L in the dispersion medium used in step b), and the cytokinin plant hormone concentration is 0 mg/L.

The carbon source concentration in the dispersion medium used in step b) is preferably at least 10 mg/L, more preferably at least 20 mg/L. The carbon source concentration is preferably not more than 50 mg/L, more preferably not more than 40 mg/L.

In step b), the cultured cell/whisker dispersion is preferably further mixed with a plasmid for introducing a foreign gene (a plasmid containing a target gene or a fragment thereof, hereinafter also referred to as "target gene or the like").

As used herein, the term "target gene" refers to a gene that is intended to be introduced into a rubber-producing plant. The target gene may be any gene that can be introduced into a rubber-producing plant so that the genetic trait of the rubber-producing plant can be modified. It may be a gene originally possessed by the rubber-producing plant into which it is to be introduced, or a gene derived from an organism other than the rubber-producing plant, or an artificially constructed gene. The artificially constructed gene may be, for example, a chimeric gene in which two or more genes are linked, or a mutant gene produced by mutation of a gene of any organism. The mutant gene may be produced, for example, by partial deletion or substitution of the bases in the DNA nucleotide sequence of a gene, or by insertion of a partial nucleotide sequence within the nucleotide sequence.

The target gene may also be a structural gene or a regulatory region. For example, it may be a structural gene that contains a transcription or translation control region, e.g. a promoter or terminator. It goes without saying that the control region gene may be any gene that can function in the rubber-producing plant into which the gene is to be introduced, and may be a gene derived from an organism of the same species as the rubber-producing plant into which the gene is to be introduced or a gene derived from an organism of a different species. Examples of such heterologous promoters include promoters generally used in fields related to genetic transformation, such as CaMV35 promoter and NOS promoter.

The target gene to be introduced into the rubber-producing plant may be a full-length gene or a fragment thereof. For example, a fragment consisting only of a functional domain of a structural gene may be introduced.

The target gene to be introduced into the rubber-producing plant is preferably, for example, a gene that is involved in the mechanism of latex biosynthesis or polyisoprene chain elongation to act on the yield or molecular weight of latex, or a gene that is involved in the biosynthesis of a protein, sugar (e.g. inositol, quebrachitol), or tocotrienol (a vitamin E compound that is also effective as a natural antioxidant) in latex to affect the yield thereof, or a gene that can produce a mutant of the protein, sugar, or tocotrienol. Moreover, by incorporating a regulatory region (e.g. a promoter) that functions in a tissue-specific manner into such a gene, it is possible to express the protein encoded by the target gene in a specific tissue of the plant.

The target gene or the like may be suitably incorporated into a vector along with a marker gene and optionally a reporter gene.

Examples of the marker gene include drug resistance genes such as kanamycin-resistance gene (nptII), hygromycin-resistance gene (hptI), and bleomycin-resistance gene. Examples of the reporter gene for determining the expression site in the plant include luciferase gene, β-glucuronidase (GUS) gene, green fluorescent protein (GFP) gene, and red fluorescent protein (RFP) gene.

The amounts of the cultured cells and whisker in the cultured cell/whisker dispersion may be selected appropriately in view of the type and amount of the plant, the amount of the plasmid used, and other factors.

For example, the mass ratio of the cultured cells to the whisker (the mass of the cultured cells/the mass of the whisker) in the cultured cell/whisker dispersion is preferably 10 to 100, more preferably 40 to 60. When it falls within the range indicated above, more suitable effects can be obtained.

The mass ratio of the plasmid to the cultured cells (the mass of the plasmid/the mass of the cultured cells) in the cultured cell/whisker dispersion is preferably 1,000 to 100,000, more preferably 10,000 to 50,000. The upper limit is still more preferably 30,000, particularly preferably 20,000. When the ratio falls within the range indicated above, more suitable effects can be obtained.

The combined concentration of the cultured cells and whisker in the cultured cell/whisker dispersion is preferably 0.1 to 10 mass %, more preferably 0.5 to 2 mass %. The upper limit is still more preferably 1 mass %. When the combined concentration falls within the range indicated above, more suitable effects can be obtained. In step b), the cultured cell/whisker dispersion, preferably containing a plasmid for introducing a foreign gene, is then subjected to centrifugation (centrifugal separation) to adhere the whisker to the cultured cells.

As used herein, the term "centrifugation" refers to a process of applying centrifugal force.

The centrifugal force during the centrifugation in step b) is preferably 3,000×g or more, more preferably 10,000×g or more, still more preferably 15,000×g or more, but is preferably 50,000×g or less, more preferably 30,000×g or less, still more preferably 21,000×g or less. When it falls within the range indicated above, more suitable effects can be obtained.

The duration of centrifugation in step b) is not particularly critical, and is preferably at least one minute, more preferably at least 2 minutes, still more preferably at least 4 minutes, but preferably not more than 15 minutes, more preferably not more than 10 minutes, still more preferably not more than 7 minutes. When it falls within the range indicated above, more suitable effects can be obtained.

The temperature during the centrifugation in step b) is not particularly critical, and is preferably 4 to 10° C. When it falls within the range indicated above, more suitable effects can be obtained.

A similar centrifugation procedure may preferably be repeated 1 to 20 times, preferably 2 to 5 times, to increase the adhesion of the whisker to the cultured cells.

Although in the above description, a plasmid for introducing a foreign gene is mixed into the cultured cell/whisker dispersion before centrifugation, a plasmid for introducing a foreign gene may be mixed into the cultured cell/whisker dispersion after centrifugation. However, in order to obtain more suitable effects, it is preferred to mix a plasmid for introducing a foreign gene into the cultured cell/whisker dispersion before centrifugation.

Step c):

Step c) following step b) includes damaging the cultured cells by the whisker under sonication and introducing a foreign gene into the cells.

Specifically, the cultured cell/whisker dispersion after centrifugation is subjected to sonication to damage the cultured cells by the whisker, followed by introducing a foreign gene into the cells. In this step, the whisker adhered to the cultured cells by centrifugation in step b) may be vibrated to perforate and damage the cells by the whisker. Then, the plasmid present in the cultured cell/whisker dispersion may enter the damaged cells so that the foreign gene can be introduced into the cells to produce transformed cells.

The centrifugation and sonication in steps b) and c) enable an increase in gene transfer efficiency.

As used herein, the term "sonication" refers to a process of irradiation with ultrasonic waves.

The frequency of the sonication is preferably 1 kHz or higher, more preferably 10 kHz or higher, still more preferably 20 kHz or higher, but is preferably 1 MHz or lower, more preferably 500 kHz or lower, still more preferably 100 kHz or lower, particularly preferably 60 kHz or lower. When it falls within the range indicated above, more suitable effects can be obtained.

The intensity of the sonication is preferably 0.01 W/cm$^2$ or higher, more preferably 0.1 W/cm$^2$ or higher, still more preferably 0.15 W/cm$^2$ or higher, but is preferably 10 W/cm$^2$ or lower, more preferably 1 W/cm$^2$ or lower, still more preferably 0.5 W/cm$^2$ or lower, particularly preferably 0.35 W/cm$^2$ or lower. When it falls within the range indicated above, more suitable effects can be obtained.

The irradiation time during the sonication is preferably at least 0.2 seconds, more preferably at least 30 seconds, still more preferably at least 50 seconds, but is preferably not more than 20 minutes, more preferably not more than 10 minutes, still more preferably not more than 5 minutes, particularly preferably not more than 2 minutes. When it falls within the range indicated above, more suitable effects can be obtained.

The sonication is preferably followed by leaving the callus for a period of time enough to permit entry and dispersion of a foreign gene into the cells. The temperature during this period is preferably 0 to 28° C., more preferably 0 to 6° C., and the duration of this period is preferably one minute to 3 hours, more preferably 5 minutes to 2 hours, still more preferably 10 minutes to one hour.

Step d):

Step d) following step c) includes restoring the damaged cells without removing the whisker. Specifically, the cultured cells damaged by sonication are restored to their normal (healthy) state by culturing the sonicated cultured cells (cultured cells adhered to the whisker) in step d). Thus, the cells can be restored via self-healing, and at the same time, the foreign gene (gene fragment containing the target gene or the like) introduced into the cells can be incorporated into the genes of the plant cells to produce stable transformed cells.

In general, when genetic transformation is performed using whisker techniques, the whisker is removed before restoring the damaged cells. In step d), however, the damaged cells are restored without removing the whisker. This enables an increase in gene transfer efficiency.

As used herein, the term "restoring" means that the cells damaged by the whisker are allowed to recover and divide.

The culturing process in step d) may be carried out in a basal medium, preferably MS medium.

The medium may be either a liquid or a solid, but liquid culture is preferred in order to facilitate supply of medium components to the total cells and obtain more suitable effects. When the medium is a liquid medium, static culture or shake culture, preferably shake culture, may be performed.

The culture temperature is preferably 0 to 40° C., more preferably 20 to 35° C. Culture may be carried out in the dark or in the light, and the illuminance is preferably 0 to 100,000 lx, more preferably 0 to 0.1 lx.

The culture time (duration of step d)) is not particularly critical, and is preferably at least 80 hours, more preferably at least 100 hours, still more preferably at least 120 hours, particularly preferably at least 140 hours, most preferably at least 160 hours, while the upper limit is not particularly critical. A duration of step d) that is longer than usual (about 48 to 72 hours) permits a further increase in gene transfer efficiency.

In step d) which excludes whisker removal, the mass ratio of the whisker to the cultured cells (the mass of the whisker/the mass of the cultured cells) is greater than usual (around 0) and is preferably 0.005 to 0.05, more preferably 0.01 to 0.03. When it falls within the range indicated above, more suitable effects can be obtained.

Step e):

Step e) following step d) includes screening transformed cells with an antibiotic. Specifically, the callus obtained in step d) is cultured in a selective culture medium containing an antibiotic. Thus, the transformed callus can be screened from the untransformed callus.

Step e) may be carried out in a conventional manner for use in genetic transformation.

In step e), the callus obtained in step d) is cultured in a selective culture medium containing an antibiotic. The culture conditions in step e) are not particularly critical as long as the conditions allow the transformed cells (callus that has acquired the target gene) to be selectively grown.

The selective culture medium may be either a liquid or a solid. When the selective culture medium is a liquid medium, static culture or shake culture may be performed.

The selective culture medium may be prepared by adding the antibiotic corresponding to the marker gene (introduced together with the target gene) to a base medium such as any of the listed basal media and modified basal media obtained by altering the composition of the basal media. It is preferred to add the antibiotic corresponding to the marker gene to MS medium, LS medium, B5 medium, or WP medium, more preferably MS medium, among others. Moreover, a plant growth hormone and/or a carbon source may be added, if necessary. Suitable plant growth hormones and carbon sources are those listed for the induction medium.

The antibiotic corresponding to the marker gene is not particularly limited, and those skilled in the art can make an appropriate selection according to the marker gene used. For example, when the marker gene used is a kanamycin-resistance gene, the callus (a mixture of transformed and untransformed callus) is cultured in a medium supplemented with kanamycin, where the transformed callus into which the target gene and kanamycin-resistance gene have been introduced can then grow, while the untransformed callus will not grow. Thus, the transformed callus can be selectively grown by culturing the mixture of transformed and untransformed callus in a medium supplemented with the antibiotic corresponding to the marker gene.

When kanamycin-resistance gene (nptII), hygromycin-resistance gene (hptI), and bleomycin-resistance gene are used as the marker gene, it is sufficient that kanamycin, hygromycin, and bleomycin, respectively, be used as the antibiotic.

In the process described above, preferably the foreign gene contains a kanamycin-resistance gene, and the antibiotic used in step e) is kanamycin (or the selective culture medium contains kanamycin). In this case, more suitable effects can be obtained.

The concentration of the antibiotic used (the antibiotic concentration in the selective culture medium) is preferably not more than 10 mg/L, more preferably not more than 8 mg/L, still more preferably not more than 6 mg/L, but is preferably at least 1 mg/L, more preferably at least 2 mg/L, still more preferably at least 3 mg/L. When it falls within the range indicated above, more suitable effects can be obtained.

When it is desired to prepare the selective culture medium as a solid medium, the medium may be converted to a solid using a solidifying agent as described for the induction medium.

The culture temperature is preferably 0 to 40° C., more preferably 10 to 36° C., still more preferably 20 to 28° C., particularly preferably 22 to 24° C. Culture may be carried out in the dark or in the light, and the illuminance is preferably 0 to 100,000 lx, more preferably 0 to 0.1 lx. The culture time is not particularly critical, but is preferably 0.5 to 10 weeks, more preferably 0.8 to 2 weeks.

When the selective culture medium is a solid medium, the solidifying agent concentration in the selective culture medium is preferably at least 0.1 mass %, more preferably at least 0.2 mass %. The solidifying agent concentration is preferably not more than 2 mass %, more preferably not more than 1.1 mass %, still more preferably not more than 0.6 mass %.

As described above, in step e) the callus (mixture of transformed and untransformed callus) obtained in step d) may be cultured in the selective culture medium to selectively grow the transformed callus, thereby screening the transformed callus from the untransformed callus.

For example, gene transfer efficiency may be determined in step e) by culturing the callus (mixture of transformed and untransformed callus) obtained in step d) and counting the number of grown callus, i.e. transformed callus, in the mixture. Specifically, it may be determined as described in EXAMPLES.

The methods described above can be used to efficiently produce transformed cells (transformed callus) of a rubber-producing plant.

Production of Transgenic Plant:

Now, methods for producing a transgenic plant will be described. The production of a transgenic plant may be performed by one of ordinary skill in the art at the time of filing the present application in view of the present disclosure by using the transformed cells (transformed callus) produced as described above, under appropriately modified conditions. Since the transformed cells are smaller than usual, they may optionally be grown to a larger size before the production of a transgenic plant.

Briefly, as described below, the transformed cells produced as above may be used to induce an adventitious embryo and then a shoot, which may then be elongated and rooted to regenerate a plant.

Regeneration-Inducing Step:

A regeneration-inducing step includes culturing the callus (transformed callus) in a regeneration-inducing medium containing a plant growth hormone and a carbon source to form an adventitious embryo and then a shoot. Since it is possible to stably form a shoot by inducing (forming) an adventitious embryo from the callus and culturing the adventitious embryo, the culture conditions in the regeneration-inducing step are not particularly critical as long as they can induce an adventitious embryo from the callus.

The regeneration-inducing medium may be prepared by adding a plant growth hormone to a base medium such as any of the listed basal media and modified basal media obtained by altering the composition of the basal media. It is preferred to add a plant growth hormone to MS medium, LS medium, B5 medium, or WP medium, more preferably MS medium, among others. Suitable plant growth hormones and carbon sources are those listed for the induction medium. It is preferred for the regeneration-inducing medium to contain an auxin plant hormone and/or a cytokinin plant hormone which are suitable for inducing an adventitious embryo.

The pH of the regeneration-inducing medium is not particularly critical, and is preferably 4.0 to 10.0, more preferably 5.6 to 6.5. The culture temperature is preferably 0 to 40° C., more preferably 20 to 36° C. Culture may be carried out in the dark or in the light, but is preferably carried out in the light for 10 to 16 hours out of 24 hours, and the illuminance of the light conditions is preferably 0 to 100,000 lx, more preferably 1,000 to 50,000 lx. The culture time is not particularly critical, but is preferably 1 to 50 weeks, more preferably 5 to 10 weeks.

For plants of the genus *Sonchus*, particularly *Sonchus oleraceus*, it is preferred that MS medium is used as the base medium for the regeneration-inducing medium and the regeneration-inducing medium has a sucrose concentration of 2 to 4 mass %, a naphthaleneacetic acid concentration of $1 \times 10^{-3}$ to 0.03 mg/L, a benzyladenine concentration of 0.8 to 1.2 mg/L, and a solidifying agent (gellan gum) concentration of 0.1 to 0.3 mass %.

For plants of the genus *Hevea*, particularly *Hevea brasiliensis*, it is preferred that MS medium is used as the base medium for the regeneration-inducing medium and the regeneration-inducing medium has a naphthaleneacetic acid concentration of 0.03 to 0.5 mg/L, a benzyladenine concentration of 0.01 to 1.2 mg/L, and a solidifying agent (gellan gum) concentration of 0.1 to 0.6 mass %.

As described above, in the regeneration-inducing step, an adventitious embryo and then a shoot can be formed by culturing the callus (transformed callus) in the regeneration-inducing medium. The shoot formed by the regeneration-inducing step may be used in the subsequent elongation step. A preferred timing for shifting to the subsequent elongation step is after rooting from the shoot has been visually observed and its stable growth has been confirmed.

Elongation Step:

An elongation step includes culturing the formed shoot in an elongation medium to elongate the shoot.

In the elongation step, for example, the shoot formed by the regeneration-inducing step may be cultured in an elongation medium to elongate the shoot. The elongation medium may be either a liquid or a solid, but solid culture is preferred because shoot elongation is facilitated by plating on the medium. When the elongation medium is a liquid medium, static culture or shake culture may be performed.

The elongation medium may be any of the listed basal media and modified basal media obtained by altering the composition of the basal media. The elongation medium is preferably a medium, more preferably MS medium, that is free from any plant growth hormone to suitably elongate the shoot. Suitable carbon sources are those listed for the induction medium.

The pH of the elongation medium is not particularly critical, and is preferably 4.0 to 10.0, more preferably 5.6 to 6.5. The culture temperature is preferably 0 to 40° C., more preferably 20 to 36° C. Culture may be carried out in the dark or in the light, but is preferably carried out in the light for 10 to 16 hours out of 24 hours, and the illuminance of the light conditions is preferably 0 to 100,000 lx, more preferably 1,000 to 50,000 lx. The culture time is not particularly critical, but is preferably 1 to 10 weeks, more preferably 5 to 10 weeks.

As described above, in the elongation step, the formed shoot can be elongated by culturing the shoot in the elongation medium. Further, not only elongation of the shoot but also formation of a new shoot can be achieved in the elongation step. The shoot elongated by the elongation step may be used in the subsequent rooting step. A preferred timing for shifting to the subsequent rooting step is after the shoot has been elongated to a size of about 2 to 3 cm.

Rooting Step:

A rooting step includes culturing the elongated shoot in a rooting medium to cause rooting.

In the rooting step, for example, the shoot elongated by the elongation step may be cultured in a rooting medium to cause rooting. The rooting medium may be either a liquid or a solid, but solid culture is preferred because rooting is facilitated by plating on the medium. When the rooting medium is a liquid medium, static culture or shake culture may be performed.

The rooting medium may be any of the listed basal media and modified basal media obtained by altering the composition of the basal media. The rooting medium is preferably a medium, more preferably B5 medium, that is free from any plant growth hormone to suitably root the shoot. Suitable carbon sources are those listed for the induction medium. The composition of the rooting medium may be the same as that of the elongation medium. Moreover, the rooting step may be omitted when rooting has already occurred in the elongation step.

The pH of the rooting medium is not particularly critical, and is preferably 4.0 to 10.0, more preferably 5.6 to 6.5. The culture temperature is preferably 0 to 40° C., more preferably 10 to 36° C., still more preferably 10 to 25° C. Culture may be carried out in the dark or in the light, but is preferably carried out in the light for 10 to 16 hours out of 24 hours, and the illuminance of the light conditions is preferably 2,000 to 25,000 lx. The culture time is not particularly critical, but is preferably 5 to 10 weeks.

As described above, in the rooting step, the elongated shoot can be rooted by culturing the shoot in the rooting medium. Thus, the rooted shoot (plantlet (transgenic plant)) can be obtained. The plantlet may be transplanted directly to soil, but is preferably transferred to and acclimatized in an artificial soil such as vermiculite before the transplantation to soil.

As described, the methods described earlier can be used to efficiently produce transformed cells (transformed callus) of a rubber-producing plant. Then, a shoot can be stably formed by inducing an adventitious embryo from the callus (transformed callus) and culturing the adventitious embryo. The formed shoot can be elongated and rooted to stably regenerate a plant (transgenic plant) from the callus (transformed callus).

EXAMPLES

The present invention is specifically described with reference to examples, but the present invention is not limited only to these.

Example 1

Step a):

<Preparation of Callus of *Hevea brasiliensis* (Induction Process)>

Leaves of *Hevea brasiliensis* were cleaned with running water for 15 minutes and then disinfected with 70% ethanol for one minute. The disinfected leaves were sterilized with a 1% sodium hypochlorite solution while stirring for 15 minutes. The sterilized leaves were washed with sterilized water three times, followed by wiping off the water with sterile paper.

The veins of the leaves were nicked with a surgical knife and then put on CIM medium (MS medium containing 2 mg/L 2,4-D (2,4-dichlorophenoxyacetic acid), 2 mg/L BA (benzyladenine), 3 mass % sucrose, and 0.22 mass % gellan gum) so that their surfaces were adhered to the medium. The leaves were cultured at 25° C. in the dark for 2 weeks to induce callus, which was then transferred to fresh CIM medium to obtain a callus (cultured cells).

Callus Fragmentation (Size Adjustment Process):

The callus was transferred onto a stainless steel mesh with an opening size of 1.0 mm put on a sterile beaker. Then, the callus was stroked gently with a spoon so that the callus passed through the mesh to obtain a small cell cluster. The small cell cluster (cultured cell cluster) was suspended in a small volume (about 25 mL) of liquid medium 1 (MS medium containing 30 mg/L sucrose and 2 mg/L 2,4-D) to obtain a cultured cell cluster suspension (callus suspension, cultured cell cluster size: 0.8 mm).

Step b):

<Preparation of Whisker Suspension>

An amount of 5 mg of potassium titanate whisker (LS20, Titan Kogyo, Ltd., average fiber diameter: 0.2-0.6 μm, average fiber length: 10-20 μm) was placed in a 1.5 mL tube, and 0.5 mL of ethanol was added, followed by leaving the tube overnight. Thereafter, the ethanol was completely evaporated to obtain the sterilized whisker. To the tube with the whisker was added 1 mL of sterilized water, and the mixture was stirred well and then centrifuged at 3,000 rpm/min for 5 minutes, followed by discharging the supernatant water, thereby washing the whisker. This washing operation was repeated three times, and 0.5 mL of liquid medium 1 was added to the resulting tube to obtain a whisker suspension.

<Preparation of Transgene>

The transgene used was pUC18 bearing a kanamycin-resistance gene (nptII). The plasmid (pUC18) was dissolved in TE buffer (10 mM Tris-HCl, 1 mM EDTA, pH 8.0) to a concentration of 1 mg/mL, and the solution was used as a transgene solution.

<Mixing of Cultured Cells with Whisker>

A volume of 250 μL of the cultured cell cluster suspension was placed in the tube containing the whisker suspension, and the mixture was stirred and then centrifuged at 1,000 rpm/min for 10 seconds to precipitate the callus and whisker, followed by discharging the supernatant to obtain a mixture of the callus and whisker.

<Mixing of Transgene>

A volume of 10 μL of liquid medium 1 was added and mixed into 20 μL of the transgene solution (containing 20 μg of the plasmid), and the mixture was added to the tube containing the mixture of the callus and whisker. The mixture of the callus and whisker with the transgene was sufficiently shaken to obtain a mixture (cultured cell/whisker dispersion).

<Process of Adhering Whisker to Cultured Cells>

Next, the tube containing the mixture (cultured cell/whisker dispersion) (the mass ratio of cultured cells to whisker (the mass of cultured cells/the mass of whisker) in the cultured cell/whisker dispersion): 50, the mass ratio of plasmid to cultured cells (the mass of plasmid/mass of cultured cells) in the cultured cell/whisker dispersion: 12500, the combined concentration of cultured cells and whisker in the cultured cell/whisker dispersion: 0.5 mass %) was subjected to centrifugation at 18,000×g for 5 minutes (at 4° C.), followed by shaking the tube again. This centrifugation and re-shaking operation was repeated three times to adhere the whisker to the cultured cells.

Step c) (Gene Transfer Process):

The tube containing the mixture (centrifuged cultured cell/whisker dispersion) obtained in step b) was placed in an ultrasonic generator (bath type, medium used: water) such that the tube was sufficiently immersed in the bath, and then irradiated with ultrasonic waves at a frequency of 40 kHz and an intensity of 0.25 W/cm$^2$ for one minute, followed by leaving the tube at 4° C. for 30 minutes. In this way, the cultured cells were damaged by the whisker, and the foreign gene was introduced into the cells.

Step d) (Cell Restoring Process):

The transfected callus (the mass ratio of whisker to cultured cells (the mass of whisker/the mass of cultured cells): 0.02) was added to a 3.5 cm dish, to which was then added 3 mL of MS medium, and the callus was cultured at 28° C. in the dark for one week (168 hours) using a rotary shaker (at 50 rpm/min) to restore the damaged cells and generate dividing cells. In this process, the whisker was not removed by washing or other means.

Step e) (Screening of Transformed Cells):

The dividing cells were cultured in MS medium containing kanamycin (5 mg/L) at 23° C. in the dark to screen the transformed callus from the untransformed callus.

Moreover, gene transfer efficiency was evaluated as follows.

The callus was subcultured twice at two to three-week intervals in the antibiotic-containing MS medium, and then the number of living callus was counted to determine gene transfer efficiency.

Gene transfer efficiency (%)=Living callus number (count)/Initial culture callus number (count)×100 wherein Initial culture callus number=60 pieces of callus.

The gene transfer efficiency of Example 1 was 30%. Thus, it was demonstrated that a method including steps a) to e) can efficiently produce transformed cells of a rubber-producing plant.

The invention claimed is:

1. A method of producing transformed cells of a *Hevea brasiliensis* plant, the method comprising the following steps a) to e):
    a) culturing a tissue fragment from a rubber-producing plant in a medium containing a plant growth hormone to obtain a 5.0 mm or smaller mass of cultured cells;
    b) dispersing the cultured cells obtained in step a) and a whisker in a liquid and then adhering the whisker to the cultured cells by centrifugation; followed by
    c) damaging the cultured cells by the whisker under sonication and introducing a foreign gene into the cells; followed by
    d) restoring the damaged cells without removing the whisker; followed by
    e) screening transformed cells with an antibiotic,
    wherein the antibiotic of step e) is kanamycin at a concentration of 10 mg/L or lower.

2. The method of producing transformed cells of a rubber-producing plant according to claim 1, wherein the whisker is made of potassium titanate.

3. The method of producing transformed cells of a rubber-producing plant according to claim 1, wherein step d) is carried out for at least 120 hours.

4. The method of producing transformed cells of a rubber-producing plant according to claim 1, wherein the cultured cells are in the form of callus.

* * * * *